US 6,721,598 B1

(12) United States Patent
Helland et al.

(10) Patent No.: US 6,721,598 B1
(45) Date of Patent: Apr. 13, 2004

(54) CORONARY SINUS CARDIAC LEAD FOR STIMULATING AND SENSING IN THE RIGHT AND LEFT HEART AND SYSTEM

(75) Inventors: John R. Helland, Saugus, CA (US); Gene A. Bornzin, Simi Valley, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 306 days.

(21) Appl. No.: 09/945,415

(22) Filed: Aug. 31, 2001

(51) Int. Cl.$^7$ ................................. A61N 1/18
(52) U.S. Cl. .......................... 607/4; 607/123
(58) Field of Search ................. 607/123, 148, 607/45, 6, 19; 600/509

(56) References Cited

U.S. PATENT DOCUMENTS

| 4,548,203 A | 10/1985 | Tacker, Jr. et al. ...... 128/419 D |
| 4,932,407 A | 6/1990 | Williams ................. 128/419 D |
| 5,111,811 A | 5/1992 | Smits ..................... 128/419 D |
| 5,174,289 A | 12/1992 | Cohen .................... 128/419 PG |

(List continued on next page.)

FOREIGN PATENT DOCUMENTS

| EP | 0813889 A2 | 12/1997 | .......... A61N/1/368 |
| WO | WO00/33914 | 6/2000 | .......... A61N/1/368 |

*Primary Examiner*—Mark Bockelman

(57) ABSTRACT

An implantable cardiac stimulation system and lead is capable of sensing electrical activity of the right and left heart and delivering stimulation pulses to the right and left heart. The system includes a single cardiac lead including a left ventricular pacing electrode, a left ventricular defibrillation electrode, a left atrial pacing electrode, a left atrial defibrillation electrode, and a right atrial pacing electrode. The system further includes a cardiac stimulation device including a pulse generator for delivering pacing pulses to any combination of the pacing electrodes, delivering defibrillation pulses to any combination of the defibrillation electrodes, and sensing electrical activity with any combination of the pacing electrodes. The lead is implantable in the coronary sinus of the heart and may further include a right atrial defibrillation coil electrode.

9 Claims, 3 Drawing Sheets

U.S. PATENT DOCUMENTS

| | | | |
|---|---|---|---|
| 5,235,978 A | 8/1993 | Hirschberg et al. | 607/5 |
| 5,267,560 A | 12/1993 | Cohen | 607/25 |
| 5,314,430 A | 5/1994 | Bardy | 607/5 |
| 5,350,404 A | 9/1994 | Adams et al. | 607/5 |
| 5,366,494 A | 11/1994 | Holleman et al. | 607/119 |
| 5,411,524 A | 5/1995 | Rahul | 607/4 |
| 5,411,529 A | 5/1995 | Hudrlik | 607/5 |
| 5,423,865 A | 6/1995 | Bowald et al. | 607/5 |
| 5,431,683 A | 7/1995 | Bowald et al. | 607/5 |
| 5,466,254 A | 11/1995 | Helland | 607/123 |
| 5,531,764 A | 7/1996 | Adams et al. | 607/5 |
| 5,545,204 A | 8/1996 | Cammilli et al. | 607/123 |
| 5,662,697 A | 9/1997 | Li et al. | 607/122 |
| 5,720,768 A | 2/1998 | Verboven-Nelissen | 607/9 |
| 5,800,465 A * | 9/1998 | Thompson et al. | 607/9 |
| 5,814,079 A | 9/1998 | Kieval | 607/4 |
| 5,814,081 A | 9/1998 | Ayers et al. | 607/5 |
| 5,836,975 A | 11/1998 | DeGroot | 607/5 |
| 5,836,976 A | 11/1998 | Min et al. | 607/6 |
| 5,865,838 A | 2/1999 | Obel et al. | 607/5 |
| 5,902,324 A | 5/1999 | Thompson et al. | 607/9 |
| 5,902,329 A | 5/1999 | Hoffmann et al. | 607/121 |
| 5,913,887 A | 6/1999 | Michel | 607/123 |
| 5,935,159 A | 8/1999 | Cross, Jr. et al. | 607/116 |
| 5,964,795 A | 10/1999 | McVenes et al. | 607/122 |
| 5,968,079 A | 10/1999 | Warman et al. | 607/5 |
| 5,978,704 A | 11/1999 | Ideker et al. | 607/5 |
| 5,987,354 A | 11/1999 | Cooper et al. | 607/5 |
| 5,999,853 A | 12/1999 | Stoop et al. | 607/9 |
| 6,006,131 A | 12/1999 | Cooper et al. | 607/5 |
| 6,041,256 A | 3/2000 | Michel | 607/5 |
| 6,055,457 A | 4/2000 | Bonner | 607/126 |
| 6,067,471 A | 5/2000 | Warren | 607/5 |
| 6,070,100 A | 5/2000 | Bakels et al. | 607/9 |
| 6,070,101 A | 5/2000 | Struble et al. | 607/9 |
| 6,070,104 A * | 5/2000 | Hine et al. | 607/123 |
| 6,081,748 A | 6/2000 | Struble et al. | 607/9 |
| 6,122,545 A | 9/2000 | Struble et al. | 607/9 |
| 6,169,921 B1 | 1/2001 | KenKnight et al. | 607/4 |
| 6,205,357 B1 | 3/2001 | Ideker et al. | 607/14 |
| 6,249,700 B1 | 6/2001 | Alt | 607/4 |
| 6,249,709 B1 | 6/2001 | Conger et al. | 607/122 |
| 6,266,563 B1 | 7/2001 | KenKnight et al. | 607/5 |
| 6,339,724 B1 | 1/2002 | Thong | 607/28 |
| 6,434,428 B1 | 8/2002 | Sloman et al. | 607/28 |
| 6,434,430 B2 | 8/2002 | Borgersen et al. | 607/122 |
| 6,456,881 B1 | 9/2002 | Bornzin et al. | 607/27 |
| 6,490,486 B1 | 12/2002 | Bradley | 607/28 |
| 6,490,489 B2 | 12/2002 | Bornzin et al. | 607/122 |
| 6,493,583 B1 | 12/2002 | Levine et al. | 607/9 |
| 6,587,720 B2 | 7/2003 | Hsu et al. | 607/4 |
| 2002/0103507 A1 | 8/2002 | Helland | 607/5 |
| 2003/0023271 A1 | 1/2003 | Hsu et al. | 607/4 |

\* cited by examiner

CORONARY SINUS CARDIAC LEAD FOR STIMULATING AND SENSING IN THE RIGHT AND LEFT HEART AND SYSTEM

RELATED APPLICATION

This application is related to copending, commonly-assigned U.S. patent applications: Ser. No. 09/910,154, filed Jul. 19, 2001, titled TWO LEAD UNIVERSAL DEFIBRILLATION SYSTEM, now abandoned; Ser. No. 09/945,449, filed Aug. 31, 2001, titled TWO LEAD UNIVERSAL DEFIBRILLATION, PACING AND SENSING SYSTEM; Ser. No. 09/944,678, filed Aug. 31, 2001, titled IMPLANTABLE CARDIAC LEAD FOR SHOCKING, PACING AND SENSING WITHIN THE LEFT HEART AND SYSTEM; Ser. No. 09/944,683, filed Aug. 31, 2001, titled CORONARY SINUS CARDIAC LEAD FOR STIMULATING AND SENSING THE ATRIA OF THE RIGHT AND LEFT HEART AND SYSTEM; Ser. No. 09/945,079, filed Aug. 31, 2001, titled THREE LEAD UNIVERSAL PACING AND SHOCKING SYSTEM; and Ser. No. 09/945,417, filed Aug. 31, 2001, titled TWO LEAD CARDIAC STIMULATION SYSTEM THAT PACES ALL FOUR CHAMBERS OF A HEART.

FIELD OF THE INVENTION

The present invention generally relates to an implantable cardiac stimulation system and lead and more particularly to such a system and lead for sensing electrical activity of the right and left heart and delivering stimulation pulses to the right and left heart. The lead is implantable in the coronary sinus region of the heart.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads and a proximal connector carried by the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the left heart, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, or cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

Universal pacing and/or defibrillation systems capable of pacing and/or defibrillating all of the chambers of the right and left heart would of course require numerous pacing and/or defibrillation electrodes to be employed within the heart and its coronary venous system. Providing the numerous electrodes to implement such universal heart stimulation systems would in turn require an inordinate number of leads if currently available right and left heart leads were employed. This would result in unduly long implant procedures and possibly more leads than the human anatomy is able to accommodate. The number of leads required may also make it difficult to accurately locate each electrode at its most efficacious position within the heart.

Hence, there is a need in the art for new and improved right and left heart leads and lead configurations which provide efficient left heart access and integrated right and left heart therapies. Electrode placement on the leads should enable effective therapy and electrode selection to accommodate differences in heart physiology from one patient to another. Universal pacing and defibrillation systems that would result from the new and improved leads and lead configurations could provide significant improved therapies. Coordinated right heart and left heart pacing therapies would be made possible. Further, improved defibrillation therapies would also be made possible. The therapies could provide improved electrode configuration selection for improved defibrillation energy distribution within the heart or support improved sequential defibrillation pulse techniques. The present invention is directed to left heart leads and right and left heart lead configurations which address the above mentioned needs.

SUMMARY OF THE INVENTION

The invention provides an implantable cardiac lead for implant in the coronary sinus of a heart and for use with an implantable cardiac stimulation device for sensing electrical activity of the right and left heart and delivering stimulation pulses to the right and left heart. The lead includes a proximal connector, a lead body including a plurality of conductors coupled to the proximal connector and insulating the plurality of conductors, a left ventricular pacing electrode for placement in electrical contact with the left ventricle, a left ventricular defibrillation electrode for placement in electrical contact with the left ventricle, a left atrial pacing electrode for placement in electrical contact with the left atrium, a left atrial defibrillation electrode for placement in electrical contact with the left atrium, and a right atrial pacing electrode for placement in electrical contact with the right atrium.

In accordance with further aspects of the invention, the lead may include a right atrial defibrillation electrode for placement in one of the right atrium and superior vena cava.

The defibrillation electrodes may be coil electrodes.

In accordance with further features of the invention, the right atrial pacing electrode of the lead is preferably positioned on the lead body so that when the left ventricular pacing electrode is adjacent the left ventricle within the coronary sinus of the heart, the right atrial pacing electrode is within the coronary sinus adjacent to the ostium of coronary sinus.

The invention further provides an implantable cardiac stimulation system capable of sensing electrical activity of the right and left heart and delivering stimulation pulses to the right and left heart. The system includes a single cardiac lead. The lead includes a left ventricular pacing electrode for placement in electrical contact with the left ventricle, a left ventricular defibrillation electrode for placement in electrical contact with the left ventricle, a left atrial pacing electrode for placement in electrical contact with the left atrium, a left atrial defibrillation electrode for placement in electrical contact with the left atrium, and a right atrial pacing electrode for placement in electrical contact with the right atrium. The system further includes a cardiac stimulation device including a pulse generator for delivering pacing pulses to any combination of the pacing electrodes, delivering defibrillation pulses to any combination of the defibrillation electrodes, and sensing electrical activity with any combination of the pacing electrodes.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Exemplary Embodiment of the Invention

Figure 1:
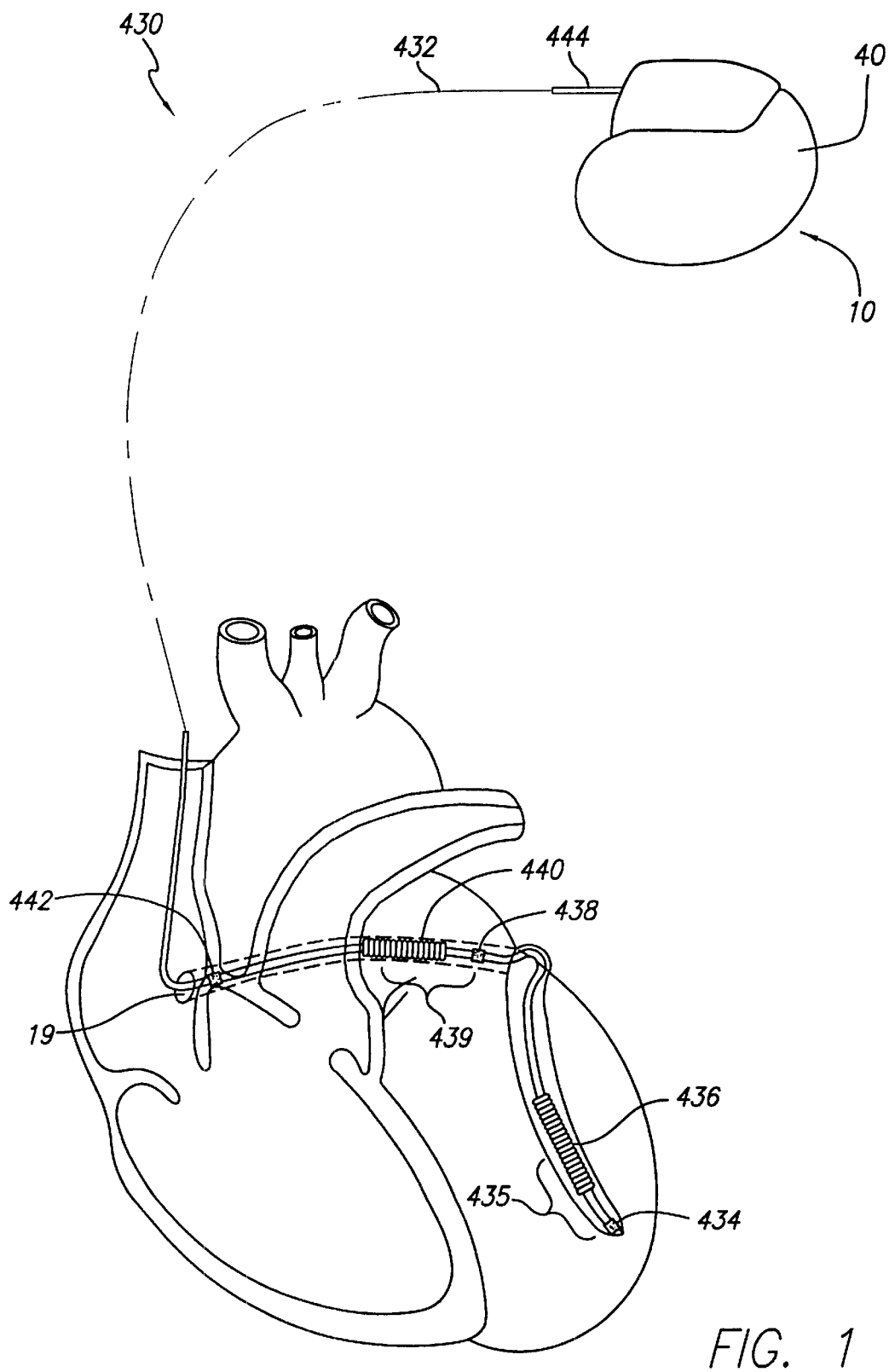
FIG. 1 is a simplified diagram of an implantable cardiac stimulation system embodying the present invention including a single lead capable of providing right atrial pacing therapy, left heart pacing therapy and left heart defibrillation therapy.

FIG. 1 shows a single lead cardiac stimulation system 430 embodying the present invention capable of providing stimulation therapy to both the right and left heart. More specifically, the system 430 of FIG. 1 is capable of providing left ventricular pacing and defibrillation therapy, left atrial pacing and defibrillation therapy, and right atrial pacing therapy.

The system 430 includes an implantable cardiac stimulation device 10 and a single implantable cardiac lead 432. The single lead 432 of the system 430 finds utility alone for providing left heart pacing and defibrillation and right atrial pacing or in conjunction with one or more additional right heart leads for providing right ventricular pacing and defibrillation therapy and right atrial defibrillation therapy.

The lead 432 is configured for implant in the coronary sinus of the left heart. The lead includes, from its distal end to its proximal end, a left ventricular tip electrode 434, a left ventricular defibrillation coil electrode 436, a left atrial sensing and pacing electrode 438, a left atrial defibrillation coil electrode 440, and a right atrial sensing and pacing electrode 442. The electrodes are spaced apart on the lead 432 such that when the left ventricular tip electrode 434 is in the distal-most end of the coronary sinus of the heart in electrical contact with and adjacent the left ventricle, the left ventricular defibrillation coil electrode 436 is in electrical contact with and adjacent the left ventricle, the left atrial sensing and pacing electrode 438 is in electrical contact with and adjacent the left atrium, the left atrial defibrillation coil electrode 440 is in electrical contact with and adjacent the left atrium, and the right atrial sensing and pacing electrode 442 is in electrical contact with and adjacent the right atrium, all of the electrodes being within the coronary sinus. Further, with respect to the right atrial sensing and pacing electrode 442, it is located on the lead 432 so that the electrode 442 is adjacent the ostium 19 of the coronary sinus within the coronary sinus. This has been found to provide effective right atrial pacing and sensing notwithstanding the fact that the lead 432 is implanted in the coronary sinus of the heart.

It should be noted that it is within the spirit of the invention to alter the order of the electrodes. For example, the ventricular electrodes may be reversed (as indicated by the arrow 435) so that the ventricular defibrillation electrode 436 may be positioned in the distal-most end of the lead. In this instance, the ventricular "tip" electrode 434 is a ring electrode which may be positioned proximal to the ventricular defibrillation electrode 452. Similarly, the left atrial sensing and pacing electrode 438 may be reversed with the left atrial defibrillation coil electrode 440, as indicated by the arrows 439, without departing from the spirit of the invention.

The lead 432 further includes a proximal connector 444 and a plurality of conductors (not shown) as known in the art for coupling the electrodes of the lead 432 to the internal circuitry of the device 10. More specifically, and with reference to FIG. 2, when the lead 432 is coupled to the device 10, the left ventricular tip electrode 434 is coupled to the left ventricular tip terminal 55, the left ventricular defibrillation coil electrode 436 is coupled to the left ventricular coil terminal 54, the left atrial sensing and pacing electrode 438 is coupled to the left atrial tip terminal 51, the left atrial defibrillation coil electrode 440 is coupled to the left atrial coil terminal 50, and the right atrial sensing and pacing electrode 442 is coupled to the right atrial tip terminal 43 of the device 10.

The system 430 of FIG. 1 may provide left ventricular sensing and pacing in a unipolar mode between the left ventricular tip electrode 434 and the conductive case 40 of the device 10 or in a bipolar mode between the left ventricular tip electrode 434 and the left ventricular defibrillation coil electrode 436. The system 430 may also provide left atrial sensing and pacing in a unipolar mode between the left atrial sensing and pacing electrode 438 and the conductive case 40 of the device 10 or in a bipolar mode between the left atrial defibrillation coil electrode 440 and the conductive case 40 of the device 10. The system 430 may further provide right atrial sensing and pacing in a unipolar mode between the right atrial sensing and pacing electrode 442 and the conductive case 40 of the device 10.

With respect to defibrillation therapy, the system 430 may provide ventricular defibrillation by applying defibrillation pulses between the left ventricular defibrillation coil electrode 436 and the conductive case 40 of the device 10. It may provide atrial defibrillation therapy by applying the defibrillation stimulation pulses between the left atrial defibrillation coil electrode 440 and the conductive case 40 of the device 10. Further, defibrillation may be accomplished by applying defibrillation pulses between the defibrillation coil electrodes 436 and 440 or in combination utilizing the conductive case 40 as a return electrode.

With respect to left ventricular pacing, it will be noted that the left ventricular tip electrode 434 and the left ventricular defibrillation coil electrode 436 reside in the distal region of the coronary sinus. This places these electrodes in a low gradient region of the heart wherein efficient pacing therapy of the left ventricle may be obtained due to the low gradient region. Further, the low gradient region promotes dissipation of remaining voltage on the left ventricle.

Further, with respect to pacing therapy, the provision of right atrial pacing and left atrial pacing may be utilized to promote homogeneity in the hemodynamics of the heart. More specifically, in a healthy heart, right atrial activations proceeds left atrial activations by a finite time of, for example, 80 to 130 milliseconds. By providing both right atrial and left atrial pacing, this right atrial to left atrial timing may be restored. Also by virtue of the ability to provide right atrial and left atrial pacing, atrial fibrillation preventative therapy such as sequential right atrial and left atrial pacing may be employed for this further purpose.

An Exemplary Cardiac Stimulation Device

Figure 2:
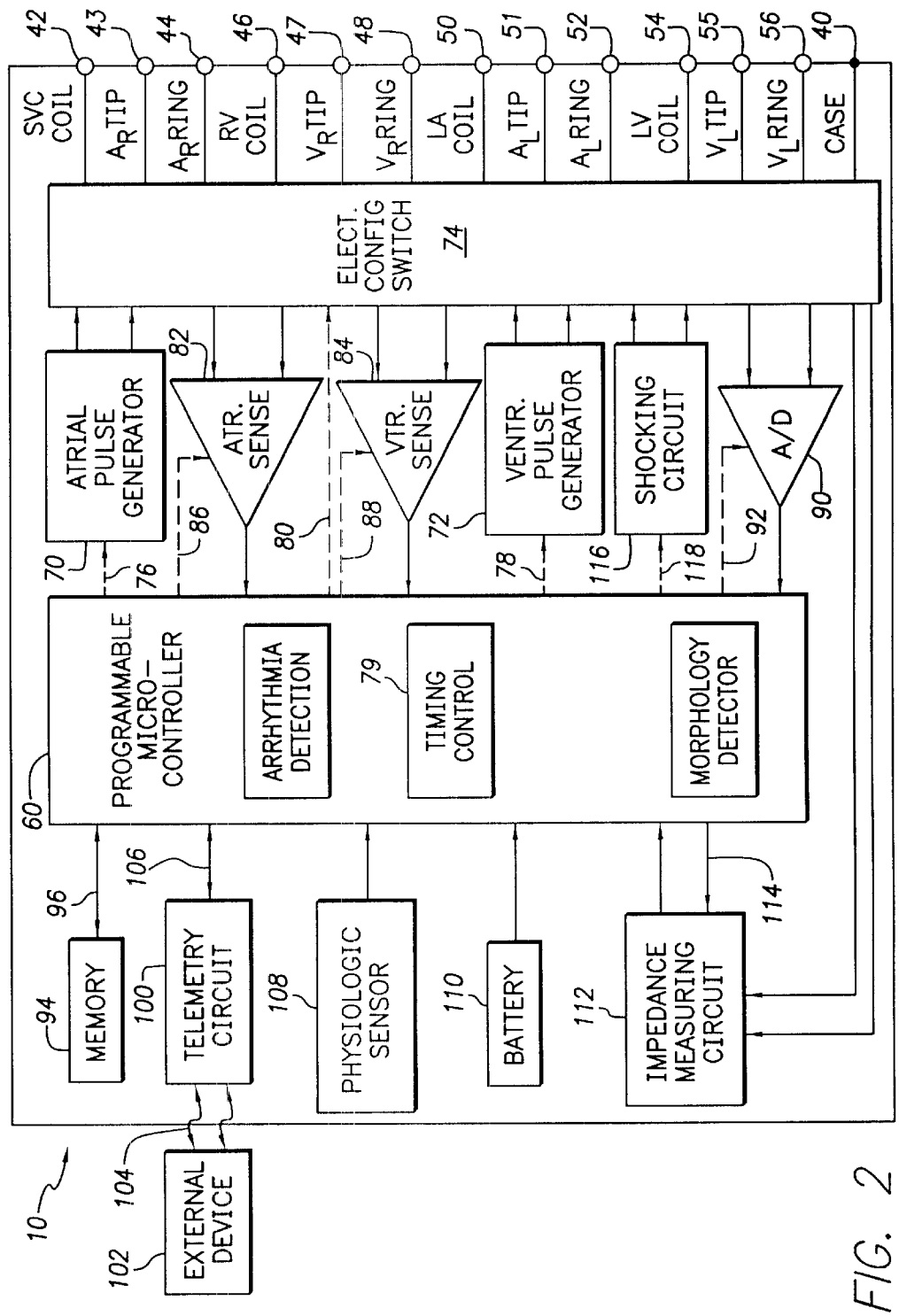
FIG. 2 is a functional block diagram of a multi-chamber implantable stimulation device which may be employed in the system of FIG. 1 which can provide cardioversion, defibrillation and pacing stimulation for all four chambers of the heart.
Figure 3:
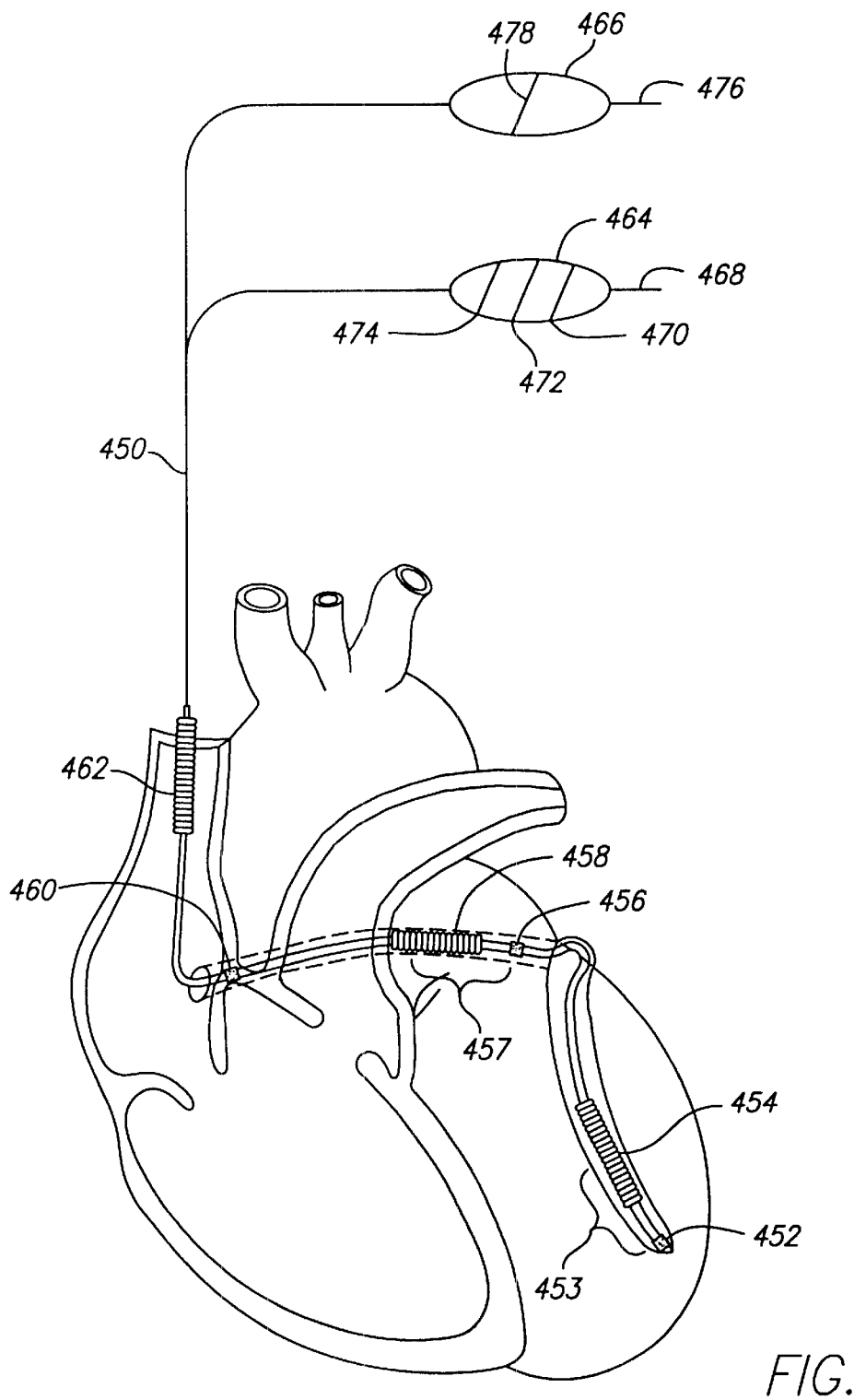
FIG. 3 is a simplified diagram of another single implantable cardiac stimulation lead embodying the present invention capable of providing right atrial pacing therapy, left heart pacing and defibrillation therapy, and right atrial defibrillation therapy.

As illustrated in FIG. 2, a simplified block diagram is shown of a multi-chamber implantable stimulation device 10 which may be employed to advantage in the system of FIG. 1 or with the lead system of FIG. 3 described herein. The device is capable of treating arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as a return stimulation electrode for all "unipolar" pacing modes. The housing 40 may further be used as a return electrode alone or in combination with one or more of the coil electrodes for shocking purposes. The housing 40 further includes a connector (not shown) having a plurality of terminals, 42, 43, 44, 46, 47, 48, 50, 51, 52, 54, 55, and 56 (shown schematically and, for convenience, the names of the electrodes to which they may be connected as appropriate are shown next to the terminals).

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses. The pacing stimulation pulses are made available as required at terminal 43 ($A_R$ TIP), terminal 44 ($A_R$ RING), terminal 47 ($V_R$ TIP), terminal 48 ($V_R$ RING), terminal 51 ($A_L$ TIP), terminal 52 ($A_L$ RING), terminal 55 ($V_L$ TIP) and terminal 56 ($V_L$ RING). The device is thus capable of providing stimulation pacing pulses for use in each of the four chambers of the heart. The atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to appropriate ones of the terminals for connection to corresponding lead electrodes for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analogto-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 may be coupled to any combination of the terminals 42–44, 46–48, 50–52, and 54–56 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 may further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. The type of sensor used is not critical to the present invention and is shown only for completeness.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown for example in FIG. 1, selected from the left atrial coil electrode 440 and the left ventricular coil electrode 436 and the housing 40 which may act as a return electrode as previously described.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

A Further Embodiment of the Invention

FIG. 3 shows a single cardiac lead 450 embodying the present invention capable of providing both pacing and defibrillation stimulation pulses to each of the right atrium, left atrium, and left ventricle. The lead 450 thus finds utility alone for providing right and left atrial and left ventricular therapy or in conjunction with one or more additional right heart leads for providing additional right ventricular pacing and/or defibrillation therapy.

The lead 450 is configured for implant in the coronary sinus of the left heart. It includes, from its distal end to its proximal end, a left ventricular tip electrode 452, a left ventricular defibrillation coil electrode 454, a left atrial sensing and pacing electrode 456, a left atrial defibrillation coil electrode 458, a right atrial sensing and pacing electrode 460, and a right atrial defibrillation coil electrode 462. The electrodes are spaced apart on the lead 450 so that when the left ventricular tip electrode 452 is in the apex of the heart in electrical contact with and adjacent to the left ventricle within the coronary sinus, the left ventricular defibrillation coil electrode 454 is in electrical contact with and adjacent the left ventricle within the coronary sinus, the left atrial sensing and pacing electrode 456 is in electrical contact with and adjacent the left atrium within the coronary sinus, the left atrial defibrillation coil electrode 458 is in electrical contact with and adjacent the left atrium within the coronary sinus, the right atrial sensing and pacing electrode 460 is in electrical contact with and adjacent the right atrium within the coronary sinus adjacent the ostium of the coronary sinus, and the right atrial defibrillation coil electrode 462 is within the superior vena cava and/or the right atrium.

It should be noted that it is within the spirit of the invention to alter the order of the electrodes. For example, the ventricular electrodes may be reversed (as indicated by the arrow 453) so that the ventricular defibrillation electrode 452 may be positioned in the distal-most end of the lead. In this instance, the ventricular "tip" electrode 454 is a ring electrode which may be positioned proximal to the ventricular defibrillation electrode 452. Similarly, the left atrial sensing and pacing electrode 456 may be reversed with a left atrial defibrillation coil electrode 458, as indicated by the arrows 457, without departing from the spirit of the invention.

The proximal end of the lead 450 is bifurcated and includes a first proximal connector 464 and a second proximal connector 466. The connector 464 includes a connection pin 468 and connection contacts 470, 472, and 474. The connector 66 466 also includes a connection pin 476 and a connection contact 478. Each of the connection contacts and connection pins is coupled to a respective given one of the electrodes by conductors (not shown) and are employed for coupling the electrodes to the internal circuitry of the implantable cardiac device. With reference to FIG. 2, when the lead 450 is coupled to the device, the left ventricular tip electrode 452 is coupled to the left ventricular tip terminal 55, the left ventricular defibrillation coil electrode 454 is coupled to the left ventricular coil terminal 54, the left atrial sensing and pacing electrode 456 is coupled to the left atrial tip terminal 51, the left atrial defibrillation coil electrode 458 is coupled to the left atrial coil terminal 50, the right atrial sensing and pacing electrode 460 is coupled to the right atrial tip terminal 43, and the right atrial defibrillation coil electrode 462 is coupled to the SVC coil terminal 42.

The cardiac lead 450 may provide sensing and pacing in the left ventricle, left atrium, and right atrium as previously described with reference to the system of FIG. 12. In addition, the lead 40 affords bipolar sensing and pacing in the right atrium. To this end, sensing and pacing in the right atrium may be accomplished with the electrode configuration including a right atrial sensing and pacing electrode 460 and the right atrial defibrillation coil electrode 462.

With respect to defibrillation therapy, the therapy modalities described in connection with the system of FIG. 1 may also be provided by the lead 450. In addition, the lead 450 provides for the application of defibrillation stimulation pulses to the right atrium utilizing the right atrial defibrillation coil electrode 462. Hence, defibrillation stimulation pulses may be applied between the right atrial defibrillation coil electrode 462 and one or more of the left ventricular defibrillation coil electrode 454, the left atrial defibrillation coil electrode 458, and the conductive case of the device. Further, and more preferably, atrial therapy may be provided by the lead 40 with the application of atrial defibrillation stimulation pulses between the right atrial defibrillation coil electrode 462 and the left atrial defibrillation coil electrode 458.

As will also be noted in FIG. 3, the left ventricular tip electrode 452 and left ventricular defibrillation coil electrode 454 reside in the low gradient region of the heart as described with reference to FIG. 1. Hence, the lead 450 affords all of the advantages in this regard as previously described with respect to the low gradient region of the heart.

The lead 450 of FIG. 3 may also be utilized to particular advantage in restoring homogeneity to the electrical activation sequence of the atria of the heart. In a healthy heart, right atrial activation precedes left atrial activation by about 80 to 130 milliseconds. Hence, in a sickheart which does not have such atrial activation sequencing, the right atria may be paced 80 to 130 milliseconds before the left atrium is paced to return homogeneity of atrial activations to the heart.

While the leads shown in FIGS. 1 and 3 show coil electrodes for the defibrillation coil electrodes 436, 440, 454 and 458, this is for illustration purposes only and, in fact, the defibrillation electrodes can be any type of defibrillation electrode, including, for example, the "split configuration" electrodes taught in U.S. application Ser. No. 09/771,388, filed Jan. 26, 2001 (Helland and Bornzin), which is hereby incorporated herein by reference.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation system capable of sensing electrical activity of the right and left heart and delivering stimulation pulses to the right and left heart, the system comprising:

a single cardiac lead including a proximal connector coupled to a plurality of conductors that separately connect a left ventricular pacing electrode for placement in electrical contact with the left ventricle, a left ventricular defibrillation electrode for placement in electrical contact with the left ventricle, a left atrial pacing electrode for placement in electrical contact with the left atrium, a left atrial defibrillation electrode for placement in electrical contact with the left atrium, and a right atrial pacing electrode for placement in electrical contact with the right atrium; and a cardiac stimulation device including a pulse generator for delivering pacing pulses to any combination of the pacing electrodes, delivering defibrillation pulses to any combination of the defibrillation electrodes, and sensing electrical activity with any combination of the pacing electrodes.

2. The system of claim 1, wherein the left ventricular defibrillation electrode and the left ventricular pacing electrode are located at a distal-most end of the lead.

3. The system of claim 2, wherein the left atrial defibrillation electrode and the left atrial pacing electrode are proximal and spaced apart from the ventricular defibrillation electrode and the left ventricular pacing electrode so as to stimulate the left atrium.

4. The system of claim 3, wherein the right atrial defibrillation electrode is proximal and spaced apart from the left atrial defibrillation electrode and the left atrial pacing electrode on the lead body so as to position the right atrial electrode adjacent to the ostium of the coronary sinus.

5. The lead of claim 4, further including a right atrial defibrillation electrode for placement in one of the right atrium or superior vena cava.

6. The system of claim 1, wherein the cardiac device includes a conductive case and wherein the pulse generator delivers pacing pulses between any combination of the pacing electrodes and the case and defibrillation pulses between any combination of the defibrillation electrodes and the case.

7. The system of claim 1, further including a right atrial defibrillation electrode for placement in one of the right atrium and superior vena cava.

8. The system of claim 7, wherein the cardiac lead includes a lead body and wherein the right atrial pacing electrode is positioned on the lead body so that when the left ventricular pacing electrode is adjacent the left ventricle within the coronary sinus of the heart, the right atrial pacing electrode is within the coronary sinus adjacent to the ostium of coronary sinus.

9. The system of claim 7, wherein the cardiac device includes a conductive case and wherein the pulse generator delivers pacing pulses between any combination of the pacing electrodes and the case and defibrillation pulses between any combination of defibrillation electrodes and the case.

* * * * *